(12) United States Patent
Chen

(10) Patent No.: US 6,613,509 B1
(45) Date of Patent: Sep. 2, 2003

(54) DETERMINATION OF BASE (NUCLEOTIDE) COMPOSITION IN DNA OLIGOMERS BY MASS SPECTROMETRY

(75) Inventor: Xian Chen, Los Alamos, NM (US)

(73) Assignee: Regents of the University of California, Los Alamos, NM (US)

( * ) Notice: Subject to any disclaimer, the term of this patent is extended or adjusted under 35 U.S.C. 154(b) by 371 days.

(21) Appl. No.: 09/273,835

(22) Filed: Mar. 22, 1999

(51) Int. Cl.⁷ .......................... C12Q 1/68; C12P 19/34; G01N 15/06; G01N 30/96; C07H 21/02
(52) U.S. Cl. .................. 435/6; 435/91.1; 435/810; 422/68; 422/69; 422/78; 422/80; 422/82.05; 536/23.1; 536/24.3
(58) Field of Search .................. 435/6, 810, 91.1; 422/68, 69, 78, 80, 82.05; 536/23.1, 24.3

(56) References Cited

U.S. PATENT DOCUMENTS 5,780,232 A * 7/1998 Arlinghaus et al. ............ 435/6
5,854,033 A * 12/1998 Lizardi ...................... 435/91.2
5,972,693 A * 10/1999 Rothberg et al. ......... 435/287.2

OTHER PUBLICATIONS

N. I. Taranenko et al., "Sequencing DNA Using Mass Spectrometry for Ladder Detection," Nucleic Acids Research 26, 2488 (1998).
Pamel F. Crain et al., "Applications of Mass Spectrometry to the Characterization of Oligonucleotides and Nucleic Acids," Current Opinion in Biotechnology 9, 25 (1998).
Paul M. Lizardi et al., "Mutation Detection and Single-Molecule Counting Using Isothermal Rolling-Circle Amplification," Nature Genetics 19, 225 (1998).
Xian Chen et al., "A PCR-Based Method for Uniform 13C/15N Labeling of Long DNA Oligomers," FEBS Lett. 436, 372 (1998).
Zhengdong Fei et al., "MALDI-TOF Mass Spectrometric Typing of Single Nucleotide Polymorphisms with Mass-Tagged ddNTPs," Nucleic Acids Res. 26, 2827 (1998).

Almut M. A. Schmidt et al., "A Single-Stranded DNA Binding Protein from S.cerevisiae Specifically Recognizes the T-Rich Strand of the Core Sequence of ARS Elements and Discriminates aganist Mutant Sequences," The EMBO J. 10, 981 (1991).
David C. Muddiman et al., "Length and Base Composition of PCR-Amplified Nucleic Acids Using Mass Measurements from Electrospray Ionization Mass Spectrometry," Anal. Chem. 69, 1543 (1997).
Karl-Friedrich Becker et al., "Single Nucleotide Polymorphisms in the Human E-Cadherin Gene," Becker et al., Hum. Genet. 96, 739 (1995).
Toshihiro Tsuneyoshi et al., "Mass Spectrometric Gene Diagnosis of One-Base Substitution from Polymerase Chain Reaction Amplified Human DNA," Rapid Commun. Mass Spectrom. 11, 719 (1997).

* cited by examiner

Primary Examiner—Gary Benzion
Assistant Examiner—Arun K. Chakrabarti
(74) Attorney, Agent, or Firm—Samuel M. Freund

(57) ABSTRACT

The determination of base (nucleotide) composition in DNA by mass spectrometry is described. Accurate and efficient analyses of the enormous pool of DNA sequences are required for; (a) validation of DNA sequences; (b) comparison of a parent (known) sequence with a related (unknown) sequence, and (c) characterization of sequence polymorphisms in various genes especially those associated with genetically inherited human diseases. The combination of stable isotope-labeling of PCR products of target sequences with analysis of the mass shifts by mass spectrometry (MS) is shown to provide such analyses, since the mass-shift due to the labeling of a single type of nucleotide (i.e., A, T, G, or C) identifies the number of that type of nucleotide in a given DNA fragment. Accurate determinations of nucleotide compositions of DNA fragments have been achieved with an accuracy of ±0.03% with respect to their known sequences. The method has also been applied to identify a known single-nucleotide polymorphism (SNP). The comparisons of nucleotide compositions determined according to the teachings of the present method among homologous sequences are useful in sequence validation, sequence comparison, and characterizations of sequences polymorphisms.

26 Claims, 3 Drawing Sheets

SEQUENCE LISTING

<160> NUMBER OF SEQ ID NOS: 3

<210> SEQ ID NO 1
<211> LENGTH: 16
<212> TYPE: DNA
<213> ORGANISM: Yeast Autonomously Replicating Sequence

<400> SEQUENCE: 1
gacattatgt ttagtc                                                           16

<210> SEQ ID NO 2
<211> LENGTH: 21
<212> TYPE: DNA
<213> ORGANISM: E-Cadherin: Wild Type

<400> SEQUENCE: 2
gacgaaatca cgctgctggt c                                                     21

<210> SEQ ID NO 3
<211> LENGTH: 21
<212> TYPE: DNA
<213> ORGANISM: E-Cadherin: Mutant

<400> SEQUENCE: 3
gacgaaatca cgttgctggt c                                                     21

DETERMINATION OF BASE (NUCLEOTIDE) COMPOSITION IN DNA OLIGOMERS BY MASS SPECTROMETRY

FIELD OF THE INVENTION

The present invention relates generally to comparing DNA sequences and, more particularly, to the use of mass spectrometry for the determination of base (nucleotide) compositions of DNA fragments. This invention was made with government support under Contract No. W-7405-ENG-36 awarded by the US Department of Energy to The Regents of The University of California. The government has certain rights in this invention.

BACKGROUND OF THE INVENTION

As the emphasis of the Human Genome Project shifts toward large-scale sequence analysis of the human genome, efficient quality control (QC) measures and rapid identification of genetic variations become increasingly important in sequencing process control, genotyping and clinical diagnosis. Analysis of a large amount of genomic sequence data requires techniques that are fast, accurate, cost-effective, and easily automated. These analyses can be efficiently accomplished by comparison of nucleotide compositions of samples from various related sources. The applications of new accurate methods to determine the nucleotide composition of oligonucleotides will avoid the intensive labor and cost involved in DNA sequencing. In the absence of a redetermination of the sequence of the target DNA region, an accurate determination of the nucleotide composition of a DNA fragment is useful for: (i) verifying the accuracy of a previously determined DNA sequence; (ii) providing low-cost error checking and proofreading of a newly determined DNA sequence, and (iii) making an efficient comparison of a known DNA sequence with a related but previously undetermined DNA sequence. For example, a comparison of the newly determined nucleotide composition with a previously determined DNA sequence will indicate variation(s) in the number of a particular type of nucleotide which implies the nature (base type) and numbers of errors in these regions. Genetic variations can also be revealed by changes in the nucleotide composition between wild-type and mutant genes. The comparison of nucleotide compositions can easily be extended to score the known single nucleotide polymorphisms (SNPs), the most common genetic variation in the eukaryotic genome.

In the past few years, mass spectrometry (MS) has emerged as a powerful alternative to the techniques of gel electrophoresis for DNA sequencing and diagnosis. Mass spectrometers produce a direct mass measurement, whereas gel electrophoresis separates ions according to their mobilities which are correlated with ion masses and charges. Electrophoresis typically takes hours, but mass spectra can be acquired in seconds or minutes in the femtomolar to picomolar range. Recently, matrix-assisted laser desorption/ionization (MALDI) time-of-flight (TOF) MS has been successfully used for fast DNA sequencing and the efficient size determination of DNA molecules. However, in spite of its high accuracy and speed, DNA sequencing by MALDI-TOF MS has an upper size range of 63–100 base pairs (bp) which is much lower than the limit of 500–1000 bp for gel electrophoresis. Coupled with Sanger sequencing reactions (See, e.g., "Sequencing DNA Using Mass Spectrometry For Ladder Detection" by N. I. Taranenko et al., Nucleic Acids Research 26, 2488 (1998), MALDI-TOF MS is employed to determine the molecular weights of Sanger ladders. Signals due to false stops, fragmentations, and unidentified peaks appear increasingly with larger DNA molecules and severely complicate the sequence assignments. By contrast, the advent of MALDI-TOF MS has made it easier to ionize intact large DNA molecules and measure their mass-to-charge ratios. Single-stranded and double-stranded polymerase chain reaction (PCR) products of 500 nucleotide (nt) in length have been detected by MALDI-TOF MS. Most recently, with optimized matrix-laser combinations that reduce DNA fragmentation, infrared MALDI mass spectra of synthetic DNA, restriction enzyme fragments of plasmid DNA, and RNA transcripts up to a size of 2180 nt have been reported with an accuracy of ±0.5–1%. Although large oligomers have been detected by MALDI-TOF MS, it is generally accepted that up to a 100 mer is routine at present. However, the potential application of MALDI-TOF MS in the determination of molecular weights of intact DNA molecules has yet to be fully explored. For a review of electrospray ionization (ESI) and MALDI-TOP MS, see "Applications Of Mass Spectrometry To The Characterization Of Oligonucleotides And Nucleic Acids" by Pamela F. Crain and James A. McCloskey, Current Opinion in Biotechnology 9, 25 (1998). Except for DNA sequencing, there is at present no technique capable of directly relating the molecular weight of a DNA molecule to its base composition.

In natural abundance, biological molecules are composed of over 99% of the isotopes, $^{12}C$, $^{14}N$, and $^{1}H$, the isotopes $^{13}C$, $^{15}N$, and $^{2}H$ (D) comprising less than 1% of the mass of such molecules. Thus, the molecular weights of biological molecules are effectively the sum of the masses of most abundant isotopes. Stable isotope enrichment or labeling results in molecules where the amounts of less abundant atomic isotope(s) are increased to artificial levels. Changing the isotopic content in a DNA molecule results in a change in the mass of the molecule without substantially altering any of its chemical or physical properties, such as charge, sequence, length or structure. If a specific type of dNTP is labeled, "mass tags" for these species can be introduced into oligonucleotides prepared by PCR or by rolling-circle amplification, and provide characteristic signatures for the labeled nucleotides in the resulting oligonucleotides. See, e.g., "Mutation Detection And Single-Molecule Counting Using Isothermal Rolling-Circle Amplification" by Paul M. Lizardi et al., Nature Genetics 19, 225 (1998). The most common labeling approach is to enrich the isotopic levels of $^{13}C$ for carbon, $^{15}N$ for nitrogen, and $^{2}H$ (D) for hydrogen atoms, since these isotopes are readily taken up by living species by cell growth.

After completion of the human genome project, there will bean even greater need for routinely comparing small segments of the genome to the reference genome. These comparisons of base (nucleotide) compositions will often be no more than 80–100 bp-long DNA fragments.

Accordingly, it is an object of the present invention to determine the base (nucleotide) composition of oligonucleotides using mass spectrometry.

Another object of the invention is to determine the base (nucleotide) composition of oligonucleotides without having to sequence the oligonucleotide.

Additional objects, advantages, and novel features of the invention will be set forth in part in the description which follows, and in part will become apparent to those skilled in the art upon examinations of the following or may be learned by practice of the invention. The objects and advantages of the invention may be realized and attained by means of the instrumentalities and combinations particularly pointed out in the appended claims.

SUMMARY OF THE INVENTION

To achieve the forgoing and other objects, and in accordance with the purposes of the present invention as embodied and broadly described herein, the method for determining the base (nucleotide) composition of an oligonucleotide hereof includes: incorporating a stable, isotope-labeled form of one of the four nucleotide units of an oligonucleotide into the oligonucleotide under investigation in place of the ordinary nucleotide therein, the other three types of nucleotides in the oligonucleotide being unlabeled; measuring the mass peak of the unlabeled oligonucleotide using mass spectrometry; measuring the mass peak of the labeled oligonucleotide using mass spectrometry; obtaining the magnitude of the mass shift between the labeled oligonucleotide and the unlabeled oligonucleotide, whereby the number of isotope-labeled nucleotides in the oligonucleotide under investigation is determined, and comparing the number of isotope-labeled nucleotides with the number of that type of nucleotide in a reference oligonucleotide.

Preferably, the step of incorporating the stable, isotope-labeled nucleotide into the oligonucleotide under investigation is achieved by polymerase chain reaction (PCR) amplification of the oligonucleotide using isotope-labeled dNTP corresponding to the isotope-labeled nucleotide.

It is also preferred that PCR primers are chosen which contain a sequence for the type IIS restriction enzyme.

Preferably also the steps of measuring the mass peak of the unlabeled oligonucleotide using mass spectrometry and measuring the mass peak of the labeled oligonucleotide using mass spectrometry are achieved using matrix-assisted laser desorption/ionization time-of-flight (MALDI-TOF) mass spectrometry or electrospray ionization (ESI) mass spectrometry.

In another aspect of the present invention in accordance with its objects and purposes, the method for determining the nucleotide composition of an oligonucleotide hereof includes: incorporating a stable, isotope-labeled form of two of the four nucleotide units of an oligonucleotide into the oligonucleotide to be determined in place of the ordinary nucleotides therein, each nucleotide having a distinct mass, the other two types of nucleotides in the oligonucleotide being unlabeled; measuring, the mass peak of the unlabeled oligonucleotide using mass spectrometry; measuring the mass peak of the labeled oligonucleotide using mass spectrometry; comparing the magnitude of the mass shift between the labeled oligonucleotide and the unlabeled oligonucleotide, whereby the number of each of the isotope-labeled nucleotides in the oligonucleotide under investigation is determined, and comparing the number of isotope-labeled nucleotides with the number of that type of nucleotide in a reference oligonucleotide.

Preferably, the step of incorporating two stable, isotope-labeled nucleotides into the oligonucleotide under investigation is achieved PCR amplification of the oligonucleotide using an isotope-labeled dNTP corresponding to each of the isotope-labeled nucleotides.

It is preferred that PCR primers are chosen which contain a sequence for the type IIS restriction enzyme.

Preferably also, the steps of measuring the mass peak of the unlabeled oligonucleotide using mass spectrometry and measuring the mass peak of the labeled oligonucleotide using mass spectrometry are achieved using matrix-assisted laser desorption/ionization time-of-flight mass spectrometry or electrospray ionization mass spectrometry.

Benefits and advantages of the present invention include the determination of the base (nucleotide) composition in oligonucleotides without using gel electrophoresis with, radioactive isotope or fluorescent labeling.

BRIEF DESCRIPTION OF THE DRAWINGS

The accompanying drawings, which are incorporated in and form part of the specification, illustrate an embodiment of the present invention and, together with the description, serve to explain the principles of the invention. In the drawings:

FIG. 2a illustrating a 16-mer PCR product having with all A nucleotides labeled with $^{13}C/^{15}N$, FIG. 2b illustrating the same 16-mer PCR product having all C nucleotides labeled with $^{13}C/^{15}N$, FIG. 2c illustrating the same 16-mer PCR product having all T nucleotides labeled with $^{13}C/^{15}N$, and FIG. 2d illustrating the same 16-mer PCR product having all G nucleotides labeled with $^{13}C/^{15}N$.

FIG. 3a shows the incorporation of $^{13}C/^{15}N$-labeled dATP in the fragment while FIG. 3b shows the incorporation of $^{13}C/^{15}N$-labeled dCTP therein.

DETAILED DESCRIPTION

Briefly, the present invention includes the generation of nucleotide-specific, stable isotope $^{13}C/^{15}N/^2H$-labeled DNA coupled with analysis of the resulting mass shifts using mass spectrometry (MS) to determine the number of each type of the labeled nucleotide. Similarly, the base composition of a PCR product from a chosen region of a DNA strand can be determined. Using this technique, base compositions of DNA fragments have been determined with an accuracy of ±0.03% with respect to their known sequences. The comparisons of base compositions among homologous sequences are useful in sequence validation, sequence comparison, and characterizations of sequence polymorphisms. In particular, the efficiency and accuracy of MALDI-TOF MS which provides analysis of molecular masses of short DNA molecules within seconds are employed to obtain the base composition of a polymerase chain reaction (PCR) product solely from its molecular weight. By incorporating stable, isotope-labeled nucleotides into oligonucleotides, "mass tags" are introduced into PCR products; that is, the substitution of any or all of $^{13}C$ for $^{12}C$, $^{15}N$ for $^{14}N$, and $^2H$ for $^1H$ leads to a mass change of the oligomer. With the presence of only one type (A, T, C, or G) of labeled nucleotide in an oligomer, the overall mass change of the oligomer corresponds to the number of the labeled nucleotides in the oligomer, the other three types of nucleotides remaining unlabeled with their masses unchanged. Typically, the differences in molecular weight of the oligonucleotide generated by such "mass tags" is in the range of 9–27 daltons (Da) per nucleotide, and can accurately be determined with current MALDI-TOF mass spectrometers for oligonucleotides less than 100 bp. It should be noted that the numbers of the labeled nucleotides is determined by resolving the mass shift per labeled nucleotide from each PCR labeling reaction rather than directly measuring the mass differences between different types of nucleotides.

The present method has been applied to the detection of single nucleotide polymorphisms (SNPs) in PCR products from a disease-related human gene by the measurement of the number change of the nucleotides involved in the SNP site.

Figure 1:
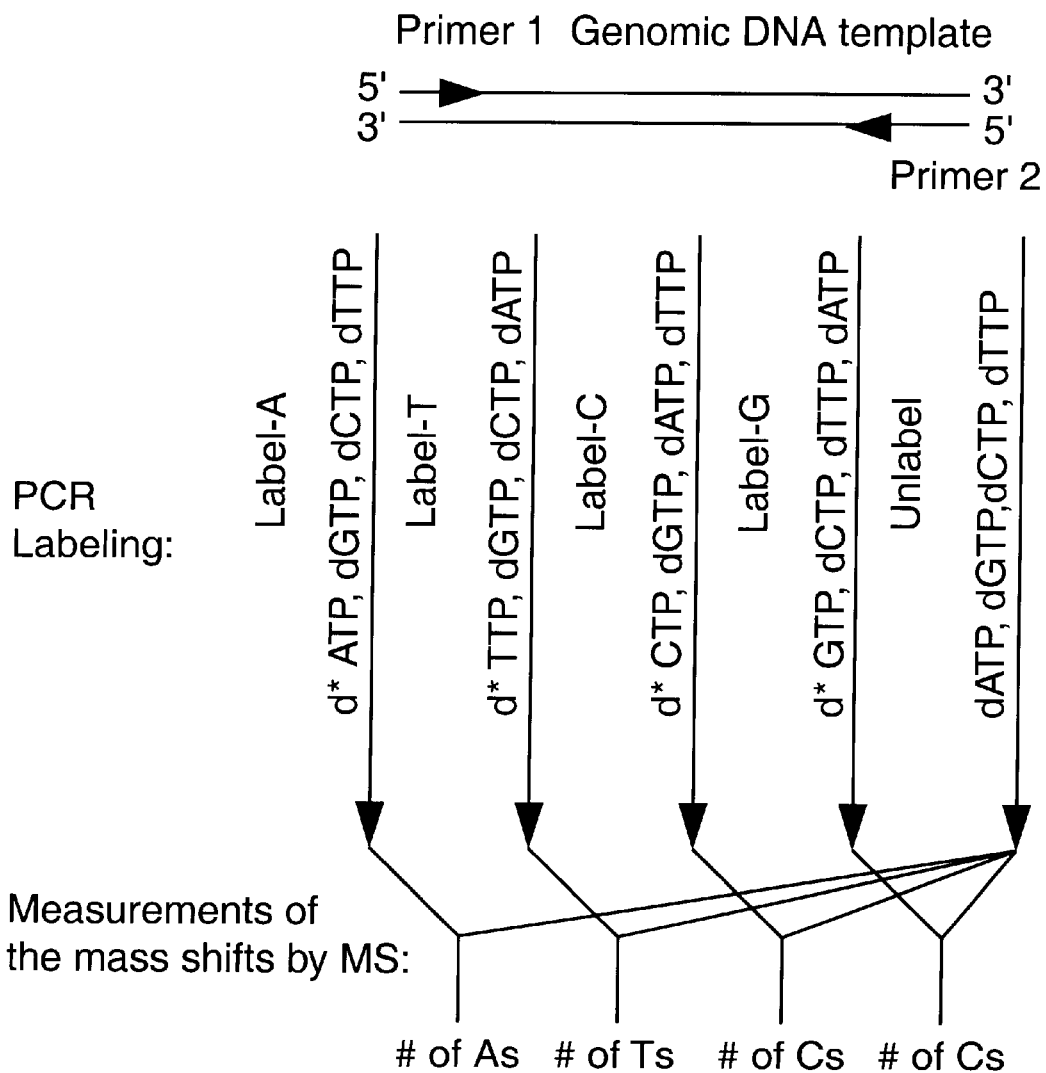
FIG. 1 is a schematic representation of the determination of nucleotide composition for each of the four bases of a oligonucleotide by multiple. PCR labeling reactions according to the teachings of the present invention, where "*" indicates stable isotope labeling.
Figure 2:
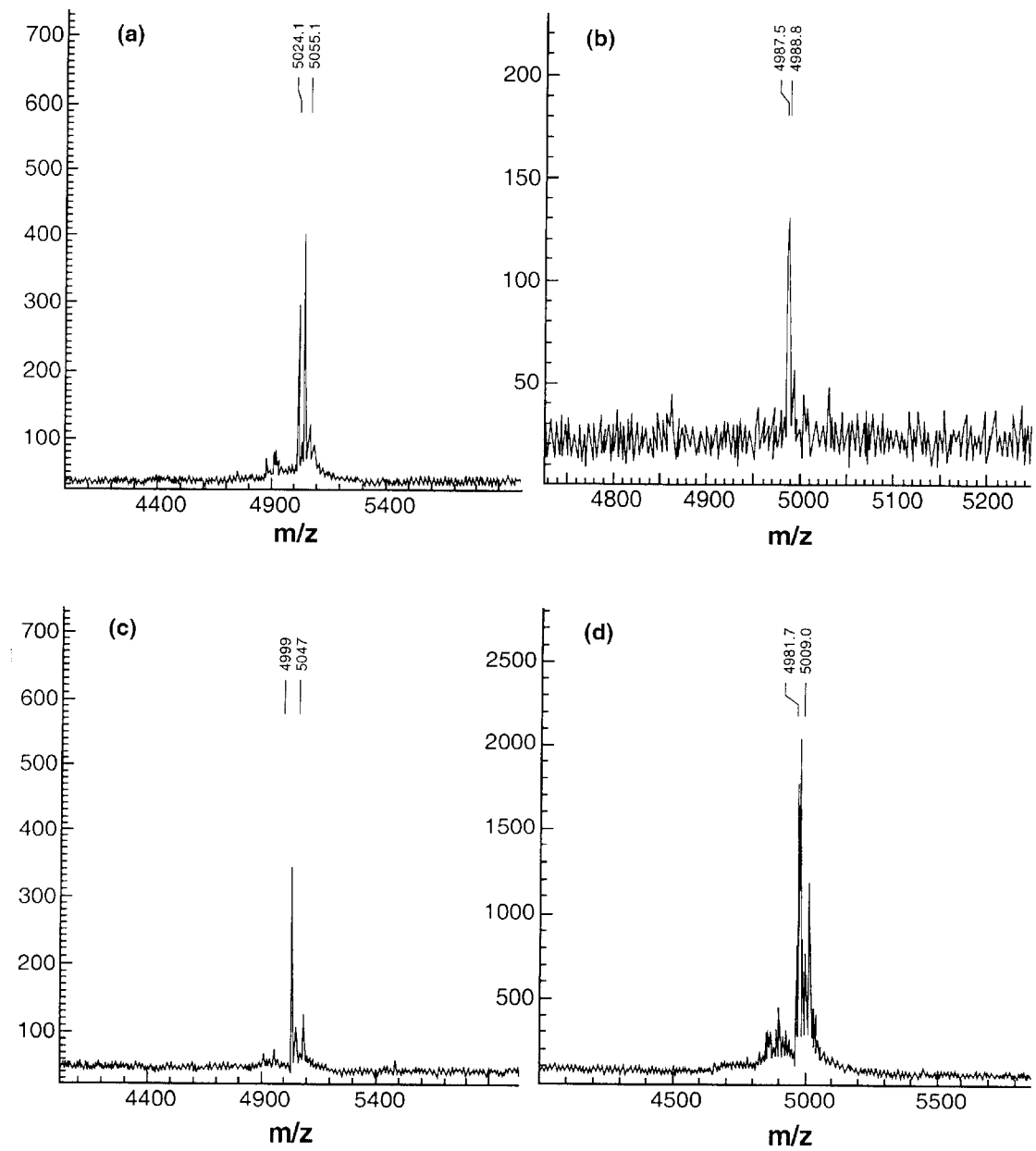
FIGS. 2a–2d are MALDI-TOF positive ion [M+H] mass spectra of PCR products with selected $^{13}C/^{15}N$ labeled nucleotides incorporated therein.

Reference will now be made in detail to the present preferred embodiments of the invention, examples of which are illustrated in the accompanying drawings. Turning to FIG. 1, the PCR reactions for introducing the "mass tags" into an oligonucleotide are schematically illustrated; one reaction employs unlabeled dNTPs as precursors, while the others show dNTPs labeled with only one type of nucleotide (i.e., dA, dT, dG, or dC). PCR amplifications of any region of interest are carried out in five separate tubes of which four tubes contain only one isotopically labeled base designated by "Label-A", "Label-T", "Label-C", and "Label-G" and three unlabeled bases, and one tube contains four unlabeled, dNTPs. The number of each type of base in the DNA can then be obtained by MS using Equation 1.

$$\frac{\text{Number of labeled bases}}{\text{in an oligomer}} = \frac{(\text{mass of labeled oligomer} - \text{mass of natural oligomer})}{\text{mass of labeled dNTP} - \text{mass of natural dNTP}} \quad \text{Eq. 1}$$

For the purpose of scoring SNP(s) with known base substitution(s), the base change can be determined by carrying out the PCR reaction(s) with only the stable isotope-labeled dNTP(s) known to be involved in the mutation. Since the occurrence frequency for SNPs is 1 out of 100 to 300 bp, SNP screening PCR fragments less than 100 bp is well within the capabilities of the present invention. Clearly, nucleotide rearrangements in the same strand, such as ATTCGT⇋TTTCGA which have the same base composition, will not be able to be distinguished. However, nucleotide rearrangements are relatively rare events.

A. Generation of each type of dNTPs Labeled with Stable Isotopes: Stable isotope $^{13}C/^{15}N/^{2}H$ labeled deoxynucleotide triphosphates (dNTPs) have been available since 1992. Stable isotope labeling requires cells to be grown on a minimal medium containing 99 % ($^{15}NH_4)_2SO_4$ or $^{15}NH_4Cl$ as the sole source of nitrogen for $^{15}N$ labeling, and/or 99% $^{13}CH_3OH$ or sodium [1,2-$^{13}C_2$, 99%] acetate as the sole carbon source for $^{13}C$ labeling, and/or 99.9% $^{2}H_2O$ as the sole deuterium source for $^{2}H$ labeling of DNA. After separation from proteins and RNA, the labeled deoxyribonucleotide monophosphates, d*NMPs (where "*" indicates a labeled nucleotide) are then enzymatically converted into the triphosphate (d*NTPs). A mixture of >99% $^{13}C$ and $^{15}N$ ($^{13}C/^{15}N$) labeled d*NTP was purchased from Martek Biosciences Corporation (Columbia, Md. 21045 USA). Four types of $^{13}C/^{15}N$ labeled nucleotides, d*ATP, d*TTP, d*CTP and d*GTP, have been separated by reverse-phase high pressure liquid chromatography (HPLC) (Vydac C18 reverse phase 218TP54 HPLC column). The selection of the isotopic species for the d*NTPs depends on the mass shift required for different lengths of the PCR products to be resolved by MS. The mass shifts generated from various combinations of labels are given in Table 1. $^{15}N$ labeling alone has not been considered due to the small numbers of nitrogen atoms (2–5) in a given nucleotide. In considering the mass tagging of nucleotides with deuterium ($^{2}H$) it should be noticed that some of the hydrogens in the nucleotides are labile. These include the amino and imino hydrogens which will exchange rapidly with deuterium in $D_2O$ solution and vice versa. Some carbon-bound $^{2}H$ (or $^{2}H$), for example, the hydrogens at the H-8 position of adenine or guanine are readily exchangeable and can migrate within the base during ionization. The hydrogens attached to the sugar ring are non-exchangeable. To generate uniformly $^{2}H$ labeled PCR products, $^{2}H$ substituted solvents (e.g., $D_2O$) should be used during PCR reactions. Mass tags generated from two categories of exchangeable and non-exchangeable deuteriums are listed in Table 1. As can be seen useful $^{2}H$ labeling of bases can be expected even in $^{2}H_2O$.

TABLE 1

Mass Shifts (Da) of Each Type of Nucleotides (Column 3–9) due to Stable Isotope Labeling

| Base | Formula | $^{13}C$ | $^{2}H$(total) | $^{2}H$/(ex/nonex) | $^{13}C/^{15}N$ | $^{13}C/^{2}H$(nonex) | $^{15}N/^{2}H$ (nonex) | $^{13}C/^{15}N/$ $^{2}H$(nonex) |
|---|---|---|---|---|---|---|---|---|
| dC | $C_9H_{12}N_3O_6P$ | 9 | 12 | 3/9 | 12 | 21(18) | 15(12) | 24(21) |
| dT | $C_{10}H_{13}N_2O_7P$ | 10 | 13 | 2/11 | 12 | 23(21) | 15(13) | 25(23) |
| dA | $C_{10}H_{12}N_5O_5P$ | 10 | 12 | 4/8 | 15 | 22(18) | 17(13) | 27(23) |
| dG | $C_{10}H_{12}N_5O_6P$ | 10 | 12 | 5/7 | 15 | 22(17) | 17(12) | 27(22) |

"total" - total numbers of deuterium substitutions including exchangeable and non-exchangeable sites; "ex" - exchangeable sites; "nonex" - non-exchangeable sites.

B. Generation of PCR products with $^{13}C/^{15}N$ labeled dNTPs: In accordance with FIG. 1, four $^{13}C/^{15}N$ labeled PCR products of the target oligonucleotide were generated, each with a labeled nucleotide. These are PCR products with; (i) >99% $^{13}C/^{15}N$-labeled dATP incorporated ("Label-A"); (ii) >99% $^{13}C/^{15}N$-labeled dTTP incorporated ("Label-T"); (iii) >99% $^{13}C/^{15}N$-labeled dCTP incorporated ("Label-C"); and (iv) >99% $^{13}C/^{15}N$-labeled dGTP-incorporated ("Label-G"). Unlabeled PCR products with all unlabeled dNTPs incorporated were also generated ("Unlabeled"), as were those with all $^{13}C/^{15}N$-labeled dNTPs incorporated ("Label-L"). The pUC19-TS DNA templates were used to produce the oligonucleotides with defined sequences and lengths (See, e.g., "A PCR-Based Method For Uniform $^{13}$C/$^{15}$N Labeling Of Long DNA Oligomers," by Xian Chen et al., FEBS Lett. 436, 372 (1998)). The PCR reactions were pre-denatured at 96° C. for 30 s before the start of the following thermal cycle: denature at 96° C. for 15 s, anneal at 50° C. for 30 s, and extension for 1 min at 72° C. For each 50 μl reaction, 3.1 μmole of amplified products were obtained. The length of oligomer was controlled by a restriction site, Hinc II, located at both ends. After PCR amplification, the target products generated by Hinc II digestion were purified from 4–20% polyacrylamide gels.

C. MALDI-TOF Mass Spectrometric Analysis: All cations in DNA samples, Na$^+$ in particular, were removed through microdialysis. An aliquot of 1 μL of the sample was mixed with 1 μL of matrix (saturated 3-hydroxypicolinic acid in a 1:1:2 mixture of water, acetonitrile and 0.1M ammonium citrate) prior to mass analysis. The samples were analyzed using a Bruker Reflex II time-of-flight (TOF) mass spectrometer (Bruker Analytical Systems, Inc.). The Bruker-Reflex II uses a nitrogen laser which generates a 3 ns pulse width at 337 nm and was operated in the reflection, positive-ion mode with an acceleration voltage of 25 kV. Spectra are typically acquired by averaging 50 laser shots (See, e.g., Z. Fei et al., Nucleic Acids Res. 26, 2827 (1998)).

Having generally described the present invention, the following EXAMPLES provide further details thereof.

EXAMPLE 1

For an initial "proof-of-principle", the mass shift of a uniformly labeled, double-stranded uniform $^{13}$C/$^{15}$N-labeled PCR product, "Label-L", was determined in order to examine the effect of maximum isotopic enrichment for an oligomer. PCR amplification of the target sequence in a plasmid, pUC19-TS, followed by restriction enzyme digestion of the amplified regions and purification, was performed according to the method of Chen et al., supra. From the analysis of these samples, it was determined; (i) that MALDI-TOF MS can accurately detect mass changes corresponding to the changes of stable isotopes in selected nucleotides in the PCR products; (ii) that the magnitude of the mass change (shift) indicates the number of labeled nucleotides; and (iii) that the effects of the isotopic distributions on peak broadening which may in turn affect the mass resolution were tolerable. Next, oligomers having known sequences and lengths were examined.

Accurate Determination of the Base Composition in a Short PCR Product:

A short 16-mer oligonucleotide of the consensus core sequence of the yeast autonomously replicating sequence (ARS) was used to determine nucleotide composition by the method of the present invention (See, e.g., A. Schmidt et al., The EMBO J. 10, 981 (1991)).

5'-GACATTATGTTTAGTC-3' (+) (SEQ ID No. 1)
3'-CTGTAATACAAATCAG-5' (−)

The expected nucleotide compositions for the individual strands of the 16-mer are $A_4T_7C_2G_3$ for the (+) strand and $A_7T_4C_3G_2$ for the (−) strand. The average molecular weights (Da) of the four different constituent nucleotides used in calculating expected molecular weights are A, 313.21; T, 304.20; C, 289.18; and G, 329.21 (See, e.g., D. C. Muddiman et al., Anal. Chem., 69,:1543 (1997)). Since there is a phosphate group, $PO_4^-$, at the 5'-end of each strand, a molecular weight of 16 Da of an oxygen atom should be added to the total molecular weights of each of the (+) and (−) strands. Therefore, a molecular weight of 4964.3 Da is expected for the (+) strand and 4951.3 Da for the (−) strand. FIGS. 2(a)–(d) show the MALDI mass spectra for the various labeled PCR products of this 16-mer. Note that under the conditions for MALDI-TOF MS, double-stranded DNA will denature, so that the majority species observed in the mass spectra correspond to the molecular weights of the two complementary single-stranded DNA oligomers. For example, in FIG. 2a, the PCR product of "Label-A" gives two mass peaks at molecular weights of 5024.1 Da and 5055.1 Da which correspond to the expected masses of 5024.3 Da and 5055.1 Da for the (+)- and (−)-strands, respectively. By comparison to the molecular weight of the unlabeled PCR product of the 16-mer, there are mass increases of 59.6 Da for the (+)-strand and 103.3 Da for the (−)-strand of the PCR product of "Label-A". These mass shifts come from the four and seven $^{13}$C/$^{15}$N labeled adenines in the (+)-strand, 5'-GACATTATGTTTAGTC-3', and (−)-strand, 3'-CTGTAATACAAATCAG-5', respectively, due to the 15 Da mass increase for each $^{13}$C/$^{15}$N labeled dATP (Table 1). Similarly, the number of each type of nucleotide was calculated from the mass differences between $^{13}$C/$^{15}$N-labeled and the unlabeled products. The calculated molecular weights, the MS determined molecular weights, and the mass shifts for each labeled strand of $^{13}$C/$^{15}$N labeled PCR products are summarized in Table 2. For the four labeled PCR products; that is, "Label-A", "Label-T", "Label-C" and "Label-G", the errors of the mass measurements are from 0.1 (in most cases) to 1.2 Da. Therefore, MALDI-TOF MS can detect stable isotopes incorporated into DNA molecules with an accuracy better than ±0.02%. The largest error of 1.8 Da observed for "Label-L" corresponds to a measurement of MALDI-TOF MS with an accuracy of ±0.03%. Based on an estimate of the line widths of the peaks at 50% maximum intensity, the mass resolution (m/Δm) of MALDI-TOF MS for this size of DNA molecule is on the order of 700–800. These results clearly show that stable isotope labeling of a nucleotide (d*NTP) creates a defined mass shift. The magnitude of these mass shifts reflects precisely the number of the incorporated $^{13}$C/$^{15}$N labeled dNTPs. From these mass shifts, the anticipated nucleotide composition of the 16-mer is accurate to within an error of ±0.03%.

TABLE 2

The Expected and the MS-Determined Molecular Weights (Found) for Each Labeled Strand of $^{13}$C/$^{15}$N Labeled PCR Products.

| PCR Product | | Label-A | Label-T | Label-C | Label-G | Label-L | Unlabeled |
|---|---|---|---|---|---|---|---|
| Total MW (Da) | Expected | 5024.3 | 5048.3 | 4988.3 | 5009.3 | 5176.3 | 4964.3(+) |
| | | 5056.3 | 4999.3 | 4987.3 | 4981.3 | 5169.3 | 4951.3(−) |
| | Found | 5024.1 | 5047.1 | 4988.8 | 5009.8 | 5174.5 | 4964.5(+) |
| | | 5055.1 | 4999.2 | 4987.5 | 4981.7 | 5168.8 | 4951.8(−) |

TABLE 2-continued

The Expected and the MS-Determined Molecular Weights (Found) for Each Labeled Strand of $^{13}$C/$^{15}$N Labeled PCR Products.

| PCR Product | Label-A | Label-T | Label-C | Label-G | Label-L | Unlabeled |
|---|---|---|---|---|---|---|
| Mass Shifts | 59.6(60) | 82.6(84) | 24.3(24) | 45.3(45) | 210(213) | 0(+) |
| (Da) Found | 103.3(105) | 47.4(48) | 35.7(36) | 29.9(30) | 217(219) | 0(−) |
| (Expected) | | | | | | |
| Number of | 4 | 7 | 2 | 3 | | (+) |
| nt | 7 | 4 | 3 | 2 | | (−) |

A short 16-mer oligonucleotide of the consensus core sequence of the yeast autonomously replicating sequence (ARS) was used for examining its nucleotide composition by the present method:
5'-GACATTATGTTTAGTC-3' (+)
3'-CTGTAATACAAATCAG-5' (−)
As shown in Table 1, mass shifts for each type of $^{13}$C/$^{15}$N labeled dNTP: 15 Da for d*ATP, 12 Da for d*TTP, 12 Da for d*CTP, and 15 Da for d*GTP.

The incorporation of selected types of nucleotides with enriched isotopes gives a non-natural isotopic distribution. One concern is whether the natural isotopic distribution introduces line-broadening and reduces mass spectrometric resolution when molecular weights of labeled oligomers are measured. Line-broadening in MALDI mass spectra may affect the accuracy of determination of the mass shifts of labeled PCR products. To test this effect, stable, isotope-labeled d*NTPs with >99% $^{13}$C- and $^{15}$N-enrichment were used. The line width for each peak of labeled and unlabeled PCR products was measured. The line width calculated from peaks of all of the PCR products of the 16-mer was in the range of 6.0–6.9; that is, the line width for mass peaks of labeled products are the same as those for peaks obtained for the naturally occurring oligomer. The data indicates that the isotopic purity of each >98% $^{13}$C/$^{15}$N-labeled dNTP is sufficiently high to maintain a line width similar to that for the naturally occurring oligomer. In addition, satellite peaks due to the natural isotopic distribution were not observed and, thus, did not interfere with the measurements.

EXAMPLE 2
Detection of a Known Single Nucleotide Polymorphism (SNP) in PCR Products:

The E-cadherin gene is a potential tumor suppresser gene encoding a calcium-dependent cell adhesion molecule crucial for establishing and maintaining epithelial integrity (K.-F. Becker et al., Hum. Genet. 96, 739 (1995)). One of four known polymorphisms in the E-cadherin cDNA is a C to T substitution at position 2797. Due to its relatively high frequency, the polymorphism at position 2797 is important for further genetic studies of the role of E-cadherin in tumor development and progression. The sequences of the PCR products of the polymorphic site are (italics indicates the restriction site of HincII):

Wild-type:
5'-GAC GAAATCACG*C*TGCTG GTC-3' (+) (SEQ ID No. 2)

(A) 3'-CTG CTTTAGTGC*G*ACGAC CAG-5' (−)

Mutant-type:
5'-GAC GAAATCACG*T*TGCTG GTC-3' (+) (SEQ ID No. 3)

(B) 3'-CTG CTTTAGTGC*A*ACGAC CAG-5' (−)

Figure 3:
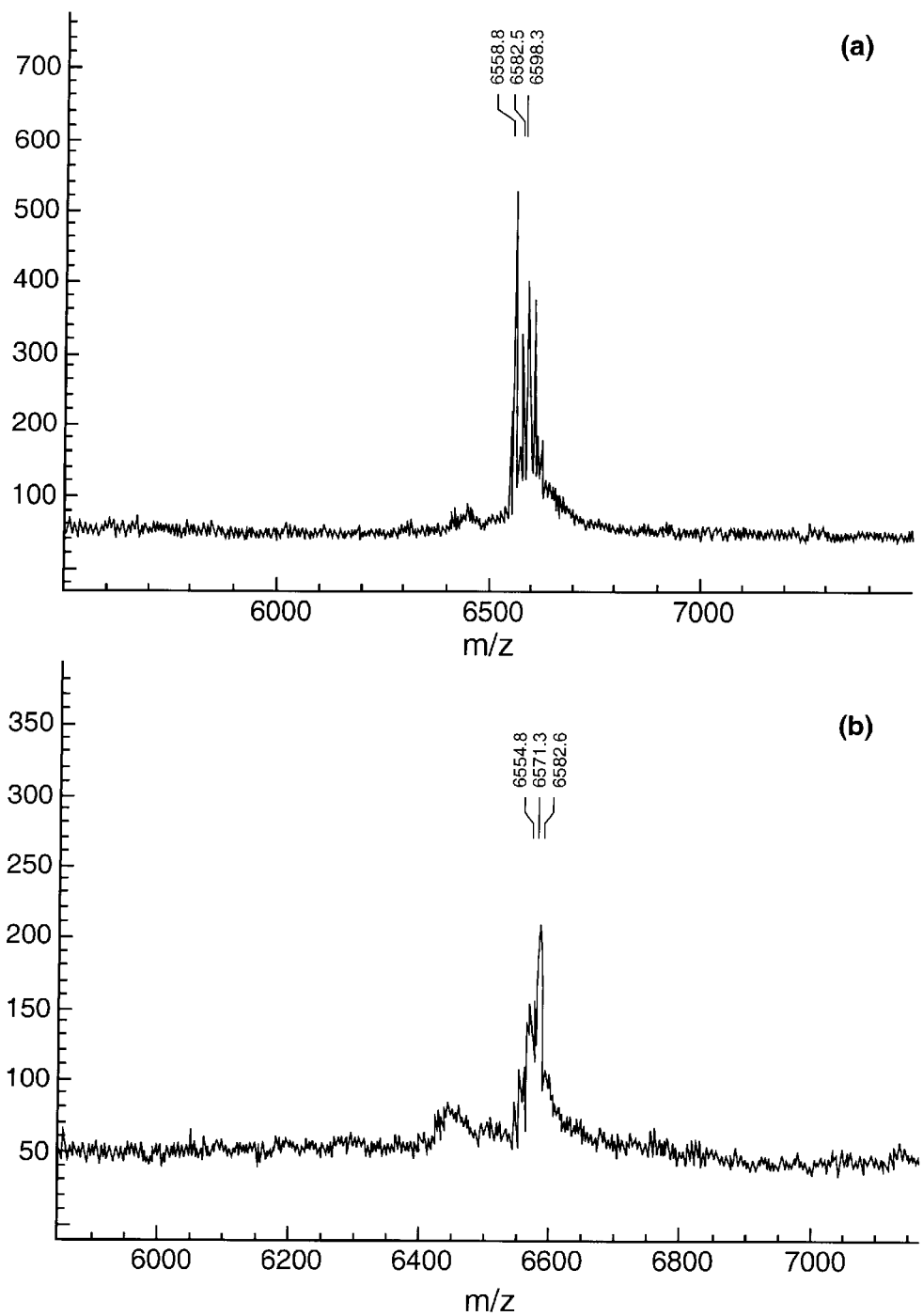
FIGS. 3a and 3b are MALDI-TOF simultaneous positive ion [M+H] mass spectra of the 21-mer PCR products of a (+)/(−) fragment of the wild-type E-cadherin gene and the same gene fragment having a polymorphic site therein where

Both the wild-type synthetic oligonucleotide (A) and the mutant-type containing the SNP (B) were inserted into the Hinc II site of pUC19 vector. The recombinant templates, pUC19-TS, were confirmed by DNA sequencing. The stable, isotopically labeled 21-mer PCR products, "Label-A" and "Label-C", respectively, were generated according to the experimental design described in FIG. 1. Since all four types of nucleotides are involved in this SNP site; that is, the base substitution, C→T in the (+)-strand, or G→A in the (−)-strand, only two PCR labeling reactions need be carried out: "Label-C" and "Label-A", respectively, with $^{13}$C/$^{15}$N-labeled d*CTP and d*ATP as precursors to type this site. After microdialysis of the gel-purified oligonucleotides, MALDI-TOF MS analysis gave the number of A nucleotides and the number of C nucleotides in each individual single-stranded DNA fragment from PCR products of "Label-C" and "Label-A". As shown in FIG. 3a, mass peaks from the 21-mer PCR products of "Label-A" of both wild-type and mutant sequences are present in the same spectrum. The mass shifts for "Label-A" or "Label-C" were found for each individual strand and are summarized in Table 3. From these values, the change in the number of a particular type of nucleotide in each strand through the incorporation of its labeled d*NTP was accurately determined. From the molecular weight measurements of the PCR products of "Label-A" (FIG. 3a), the number of A nucleotides in the (−) wild-type and mutant strands are four and five, respectively, (indicated in Bold in Table 3). Similarly, using "Label-C" (FIG. 3b), the change in the number of C nucleotides is from six in the (+) strand of the wild-type to five in the (+) strand of the mutant-type (indicated in Bold in Table 3). Therefore, using this method the single nucleotide change of C→T in (+) strand and the corresponding G→A can be accurately determined. It should be mentioned that the small unassigned peaks in these spectra correspond to the naturally abundant oligomer, and Na$^+$ adducts thereof.

TABLE 3

The Expected and the Mass-Spectrometrically Determined Molecular Weights (Found) for Each Strand of $^{13}$C/$^{15}$N-Labeled PCR Products of the 21-mer-Containing SNP.

| | Wild-Type | | Mutant | |
|---|---|---|---|---|
| | (+) | (−) | (+) | (−) |
| Base Composition Label-A MW (Da) | $A_5T_4C_6G_6$ | $A_4T_5C_6G_6$ | $A_5T_5C_5G_6$ | $A_5T_5C_6G_5$ |
| Expected MW (Da) | 6584.2 | 6560.2 | 6599.2 | 6559.2 |
| Found MW (Da) | 6582.5 | 6558.8 | 6598.3 | 6558.8 |
| Mass Shifts (Da) | 73.3 | 58.6 | 74.1 | 74.6 |
| | (75) | (60) | (75) | (75) |
| Number of A | 5 | 4 | 5 | 5 |

TABLE 3-continued

The Expected and the Mass-Spectrometrically Determined Molecular Weights (Found) for Each Strand of $^{13}$C/$^{15}$N-Labeled PCR Products of the 21-mer-Containing SNP.

|  | Wild-Type | | Mutant | |
|---|---|---|---|---|
|  | (+) | (−) | (+) | (−) |
| Label-C MW (Da) | | | | |
| Expected MW (Da) | 6581.2 | 6572.2 | 6584.2 | 6556.2 |
| Found MW (Da) | 6582.6 | 6571.3 | 6582.6 | 6554.8 |
| Mass Shifts (Da) | 73.4 | 71.1 | 58.4 | 70.6 |
|  | (72) | (72) | (60) | (72) |
| Number of C | 6 | 6 | 5 | 6 |

As shown in Table 1, mass shifts for each type of $^{13}$C/$^{15}$N labeled dNTP: 15 Da for d*ATP, 12 Da for d*CTP. MW-molecular weight.
MW for unlabeled strands of wild-type: 6509.2 Da (+) and 6500.2 Da (−); Mutant-type: 6524.2 Da (+) and 6484.2 Da (−).

Current MS methods to detect SNPs are through resolving the mass differences due to single base substitutions (See, e.g., T. Tsuneyoshi et al., Rapid-Commun. Mass Spectrom. 11, 719 (1997)). However, routine MS instruments can only measure masses of oligonucleotides with an accuracy of 0.02–0.08% (<70 mer). This implies that single-stranded DNA must be shorter than 60 nucleotides in order to resolve the mass difference of 9 Da due to the A→T single-base conversion. With stable isotopic labeling, a mass shift of 9–27 Da per nucleotide is generated according to the teachings of the present invention, depending upon the combination of isotopes enriched in a nucleotide (Table 1). The present method for detecting DNA sequence variations, by contrast, is based on the accurate measurement of molecular weight differences between unlabeled and labeled PCR products. Note that stable isotope labeling does not change the length, sequence or other physical properties of the DNA molecules except for their masses. The incorporation of $^{13}$C/$^{15}$N/$^2$H triply labeled d*NTPs increases the magnitude of the mass resolution by a factor of 3 with respect to the mass differences between nucleotides. Therefore, with the same mass accuracy of 0.02–0.08%, the technique of stable-isotope labeling has the potential to extend the MS detection of single nucleotide changes to DNA fragments of about 150–200 nucleotides within the limits of mass resolution and accuracy of current mass spectrometers. The value of the mass shift is unaffected by the charge. Due to instrumental limitations, the present method is limited to DNA fragments <70 mer. However, larger DNA molecules (>70 mer) can be digested to produce shorter PCR fragments within the allowed size limit of MS. Additionally, the use of rolling-circle amplification (See, e.g., Lizardi et al., supra) permits a reduction in the strand size produced in the PCR amplification process.

EXAMPLE 3

For a truly efficient analysis procedure, it is necessary to reduce the number of PCR labeling reactions and streamline purification for the purpose of cost-effectiveness and high throughput analysis. Although, theoretically, the five PCR reactions listed above are needed for each sample to determine the number of each of the four types of nucleotides, the following approach can be used to eliminate unnecessary reactions. As shown in Table 1, more than one atom can be labeled in a nucleotide. Therefore, enrichment with a different combination of isotopes in different types of dNTPs can introduce mass shifts characteristic of each labeled nucleotide. The enrichment of; 1) all carbon and nitrogen atoms with $^{13}$C/$^{15}$N in dATP will generate a mass shift of 15 daltons; 2) all carbon and hydrogen atoms with $^{13}$C/$^2$H in dTTP a mass shift of 23 daltons, and 3) all nitrogen and hydrogen atoms with $^{15}$N/$^2$H in dCTP a mass shift of 17 daltons, etc. Using two labeled dNTPs simultaneously, e.g., $^{13}$C/$^{15}$N labeled dATP and $^{13}$C/$^2$H labeled dTTP in one PCR reaction, designated "Label-AT" and $^{15}$N/$^2$H labeled dCTP and $^{13}$C/$^{15}$N/$^2$H labeled dGTP for another PCR reaction, designated "Label-GC", the number of each of the four types of nucleotides can be determined. Double-stranded PCR products melt to single strands of DNA under mass spectrometric conditions so that the molecular weights and mass shifts of the two complementary single-stranded DNAs can be measured. In the duplex form, the total number of As in one strand should be equal to the total number of Ts of its complementary strand, and C should be equal to G. The number of A, T, C, and Gs can then be determined from the following relationships:

| "Label-AT" | a A + t T = mass shift of coding strand |
| | a A' + t T' = mass shift of non-coding strand |
| | A = T' and T = A' |
| "Label-GC" | c C + g G = mass shift of coding strand |
| | c C' + g G' = mass shift of non-coding strand |
| | C = G' and G = C' | a, t, c, and g represent the characteristic mass shifts of each labeled dA, dT, dC and dG, respectively. A and A' represent the numbers of base A in coding, noncoding strand, respectively. Same for T and T', C and C', G and G'.

With these relationships, the number of PCR labeling reactions can be reduced from five to three; one reaction which produces strands labeled with AT, another reaction which produces strands labeled with GC, and an unlabeled reaction. In addition, if the total number of nucleotides is known for the PCR amplified region only one labeling reaction with four different values of mass shifts for each type of dNTPs is needed.

The genotyping of a single SNP site shows that the present method can also be used to type a gene fragment containing multiple single-base variants. It will be necessary to carry out multiple complimentary PCR reactions to determine the number change for each type of nucleotide involved in these SNP sites. For example, if a C→T and G→A base change coexist in the same gene product, PCR products of "Label-CG" and "Label-AT" will have to be generated, as described above. As long as the labeled products of each individual strand are correctly assigned, the type(s) and number of the nucleotides involved in these SNP sites will be able to be determined.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining the nucleotide composition of an oligonucleotide which comprises the steps of:
   (a) incorporating a stable, isotope-labeled form of one of the four nucleotide units of an oligonucleotide into the oligonucleotide under investigation in place of the ordinary nucleotide therin, the other three types of nucleotides in the oligonucleotide being unlabeled;
   (b) measuring the mass peak of the unlabeled oligonucleotide using mass spectrometry;
   (c) measuring the mass peak of the labeled oligonucleotide using mass spectrometry;
   (d) obtaining the magnitude of the mass shift between the labeled oligonucleotide and the unlabeled oligonucleotide, whereby the number of isotope-labeled nucleotides in the oligonucleotide under investigation is determined; and
   (e) comparing the number of isotope-labeled nucleotides with the number of that type of nucleotide in a reference oligonucleotide.

2. The method for determining the nucleotide composition of an oligonucleotide as described in claim 1, wherein said step of incorporating the stable, isotope-labeled nucleotide into the oligonucleotide under investigation is achieved by polymerase chain reaction amplification of the oligonucleotide using isotope-labeled dNTP corresponding to the isotope-labeled nucleotide.

3. The method for determining the nucleotide composition of an oligonucleotide as described in claim 2, wherein primers are chosen to isolate the oligonucleotide under investigation from a larger oligonucleotide strand.

4. The method for determining the nucleotide composition of an oligonucleotide as described in claim 3, wherein the chosen primers contain a sequence for the type IIS restriction enzyme.

5. The method for determining the nucleotide composition of an oligonucleotide as described in claim 1, wherein said step of incorporating a stable, isotope-labeled form of one of the four nucleotide units of an oligonucleotide into the oligonucleotide under investigation in place of the ordinary nucleotide therein is achieved using isothermal rolling-circle amplification.

6. The method for determining the nucleotide composition of an oligonucleotide as described in claim 1, wherein said steps of measuring the mass peak of the unlabeled oligonucleotide using mass spectrometry and measuring the mass peak of the labeled oligonucleotide using mass spectrometry are achieved using spectrometry techniques selected from the group consisting of matrix-assisted laser desorption/ionization time-of-flight mass spectrometry and electrospray ionization mass spectrometry.

7. The method for determining the nucleotide composition of an oligonucleotide as described in claim 1, wherein the number of labeled nucleotides in the oligonucleotide under investigation is equal to:

(the mass of the labeled oligonucleotide–the mass of the unlabeled oligonucleotide)/(the mass of the labeled dNTP–the mass of the unlabeled dNTP).

8. A method for determining the nucleotide composition of an oligonucleotide which comprises the steps of:
   (a) incorporating a stable, isotope-labeled form of two of the four nucleotide units of an oligonucleotide into the oligonucleotide under investigation in place of the ordinary nucleotides therein, each nucleotide having a distinct mass, the other two types of nucleotides in the oligonucleotide being unlabeled;
   (b) measuring the mass peak of the unlabeled oligonucleotide using mass spectrometry;
   (c) measuring the mass peak of the labeled oligonucleotide using mass spectrometry;

(d) obtaining the magnitude of the mass shift between the labeled oligonucleotide and the unlabeled oligonucleotide, whereby the number of each of the isotope-labeled nucleotides in the oligonucleotide under investigation is determined; and (e) comparing the number of isotope-labeled nucleotides with the number of that type of nucleotide in a reference oligonucleotide.

9. The method for determining the nucleotide composition of an oligonucleotide as described in claim 8, wherein said step of incorporating two stable, isotope-labeled nucleotides into the oligonucleotide under investigation is achieved by polymerase chain reaction amplification of the oligonucleotide using an isotope-labeled dNTP corresponding to each of the isotope-labeled nucleotides.

10. The method for determining the nucleotide composition of an oligonucleotide as described in claim 9, wherein primers are chosen to isolate the oligonucleotide to be sequenced from a larger oligonucleotide strand.

11. The method for determining the nucleotide composition of an oligonucleotide as described in claim 10, wherein the chosen primers contain a sequence for the type IIS restriction enzyme.

12. The method for determining the nucleotide composition of an oligonucleotide as described in claim 8, wherein said step of incorporating a stable, isotope-labeled form of one of the four nucleotide units of an oligonucleotide into the oligonucleotide under investigation in place of the ordinary nucleotide therein is achieved using isothermal rolling-circle amplification.

13. The method determining the nucleotide composition of an oligonucleotide as described in claim 8, wherein said steps of measuring the mass peak of the unlabeled oligonucleotide using mass spectrometry and measuring the mass peak of the labeled oligonucleotide using mass spectrometry are achieved using spectrometry techniques selected from the group consisting of matrix-assisted laser desorption/ ionization time-of-flight mass spectrometry and electrospray ionization mass spectrometry.

14. A method for detecting polymorphisms in oligonucleotides which comprises the steps of:

(a) incorporating a stable, isotope-labeled form of one of the four nucleotide units of an oligonucleotide into the oligonucleotide under investigation in place of the ordinary nucleotide therein, the other three types of nucleotides in the oligonucleotide being unlabeled;

(b) measuring the mass peak of the unlabeled oligonucleotide using mass spectrometry;

(c) measuring the mass peak of the labeled oligonucleotide using mass spectrometry; and (d) obtaining the magnitude of the mass shift between the labeled oligonucleotide and the unlabeled oligonucleotide, whereby the number of isotope-labeled nucleotides in the oligonucleotide under investigation is determined.

15. The method for detecting polymorphisms in oligonucleotides as described in claim 14, wherein said step of incorporating the stable, isotope-labeled nucleotide into the oligonucleotide under investigation is achieved by polymerase chain reaction amplification of the oligonucleotide using isotope-labeled dNTP corresponding to the isotope-labeled nucleotide.

16. The method for detecting polymorphisms in oligonucleotides as described in claim 15, wherein primers are chosen to isolate the oligonucleotide under investigation from a larger oligonucleotide strand.

17. The method for detecting polymorphisms in oligonucleotides as described in claim 16, wherein the chosen primers contain a sequence for the type IIS restriction enzyme.

18. The method for detecting polymorphisms in oligonucleotides as described in claim 14, wherein said step of incorporating a stable, isotope-labeled form of one of the four nucleotide units of an oligonucleotide into the oligonucleotide under investigation in place of the ordinary nucleotide therein is achieved using isothermal rolling-circle amplification.

19. The method for detecting polymorphisms in oligonucleotides as described in claim 14, wherein said steps of measuring the mass peak of the unlabeled oligonucleotide using mass spectrometry and measuring the mass peak of the labeled oligonucleotide using mass spectrometry are achieved using spectrometer techniques selected from the group consisting of matrix-assisted laser desorption/ ionization time-of-flight mass spectrometry and electrospray ionization mass spectrometry.

20. The method for detecting polymorphisms in oligonucleotides as described in claim 14, wherein the number of labeled nucleotides in the oligonucleotide under investigation is equal to:

$$(\text{the mass of the labeled oligonucleotide} - \text{the mass of the unlabeled oligonucleotide})/(\text{the mass of the labeled dNTP} - \text{the mass of the unlabeled dNTP});$$

whereby the detection of polymorphisms in the oligonucleotide under investigation is accomplished by comparing the number of labeled nucleotides with number of such nucleotides known to be present in the oligonucleotide under investigation.

21. A method for detecting polymorphisms in oligonucleotides which comprises the steps of:

(a) incorporating a stable, isotope-labeled form of two of the four nucleotide units of an oligonucleotide into the oligonucleotide under investigation in place of the ordinary nucleotides therein, each nucleotide having a distinct mass, the other two types of nucleotides in the oligonucleotide being unlabeled;

(b) measuring the mass peak of the unlabeled oligonucleotide using mass spectrometry;

(c) measuring the mass peak of the labeled oligonucleotide using mass spectrometry; and (d) comparing the magnitude of the mass shift between the labeled oligonucleotide and the unlabeled oligonucleotide, whereby the number of each of the isotope-labeled nucleotides in the oligonucleotide under investigation is determined.

22. The method for detecting polymorphisms in oligonucleotides as described in claim 21, wherein said step of incorporating two stable, isotope-labeled nucleotides into the oligonucleotide under investigation is achieved by polymerase chain reaction amplification of the oligonucleotide using an isotope-labeled dNTP corresponding to each of the isotope-labeled nucleotides.

23. The method for detecting polymorphisms in oligonucleotides as described in claim 22, wherein primers are chosen to isolate the oligonucleotide under investigation from a larger oligonucleotide strand.

24. The method for detecting polymorphisms in oligonucleotides as described in claim 23, wherein the chosen primers contain a sequence for the type IIS restriction enzyme.

25. The method for detecting polymorphisms in oligonucleotides as described in claim 21, wherein said step of incorporating a stable, isotope-labeled form of one of the four nucleotide units of an oligonucleotide into the oligonucleotide under investigation in place of the ordinary nucleotide therein is achieved using isothermal rolling-circle amplification.

26. The method for detecting polymorphisms in oligonucleotides as described in claim 21, wherein said steps of measuring the mass peak of the unlabeled oligonucleotide using mass spectrometry and measuring the mass peak of the labeled oligonucleotide using mass spectrometry are achieved using matrix-assisted laser desorption/ionization time-of-flight mass spectrometry or electrospray ionization mass spectrometry.

* * * * *